(12) United States Patent
Bougamont et al.

(10) Patent No.: US 6,516,795 B1
(45) Date of Patent: Feb. 11, 2003

(54) NOSE SPRAYER

(75) Inventors: Jean-Louis Bougamont, Eu (FR); Jean-Pierre Alleard, Eu (FR); David Leuliet, Mers-les-Bains (FR)

(73) Assignee: Rexam Sofab, Le Treport (FR)

( * ) Notice: Subject to any disclaimer, the term of this patent is extended or adjusted under 35 U.S.C. 154(b) by 0 days.

(21) Appl. No.: 09/530,958

(22) PCT Filed: Nov. 16, 1998

(86) PCT No.: PCT/FR98/02434
§ 371 (c)(1),
(2), (4) Date: May 17, 2000

(87) PCT Pub. No.: WO99/25408
PCT Pub. Date: May 27, 1999

(30) Foreign Application Priority Data

Nov. 17, 1997 (FR) .......................................... 97 14355

(51) Int. Cl.$^7$ ............................................. A61M 11/00
(52) U.S. Cl. ............................ 128/200.14; 128/200.22; 128/203.12; 604/94.01; 604/275
(58) Field of Search ....................... 128/200.21, 205.15, 128/200.11, 200.14, 200.19, 200.18, 203.23, 200.22, 203.15, 203.12; 604/94, 58, 36, 37, 94.01, 275; 222/92, 94, 96, 206, 478, 488, 566, 635; 239/86, 590.5; D23/213, 223, 225

(56) References Cited

U.S. PATENT DOCUMENTS

| | | | | |
|---|---|---|---|---|
| 1,105,934 A | * | 8/1914 | Stevens | 128/203.12 |
| 4,801,093 A | * | 1/1989 | Brunet et al. | 239/490 |
| 5,224,471 A | * | 7/1993 | Marelli et al. | 128/200.14 |
| 5,433,353 A | * | 7/1995 | Flinn | 222/481 |
| 5,683,361 A | * | 11/1997 | Elk et al. | 604/58 |
| 5,810,004 A | * | 9/1998 | Ohki et al. | 128/203.15 |
| 5,899,202 A | * | 5/1999 | Ohki et al. | 128/200.14 |
| 5,901,703 A | * | 5/1999 | Ohki et al. | 128/203.12 |
| 5,906,198 A | * | 5/1999 | Flickinger et al. | 128/200.21 |
| 5,961,489 A | * | 10/1999 | Hirota | 604/94 |
| 5,989,217 A | * | 11/1999 | Ohki et al. | 604/94 |

FOREIGN PATENT DOCUMENTS

WO   WO-92/21404 A1 * 12/1992 ............ 128/203.12

* cited by examiner

Primary Examiner—Glenn K. Dawson
(74) Attorney, Agent, or Firm—Bacon & Thomas, PLLC

(57) ABSTRACT

A nasal spray device for dispensing a liquid from a pressurized container (R). The nasal spray device includes two juxtaposed applicators (1a, 1b), each being provided with at least one expulsion duct (10a, 10b) opening at an outer end in a spay nozzle (B) and communicating at an inner end with the container (R) with a pressurizing device (P). The applicators are fixed to a base (2) which couples them to the container (R). The nasal spray device includes a first part (I) supporting the applicators (1a, 1b) and an outer bottom skirt (11) radially clamping onto a cylindrical inner bearing surface (21) provided along a surface of a second part (II) carrying the base (2). The first and second parts (II) define bottom portions of the expulsion ducts (10a, 10b).

6 Claims, 2 Drawing Sheets

NOSE SPRAYER

BACKGROUND OF THE INVENTION

The present invention relates to a nasal spray device, and more particularly to an improvement of the dispenser head of such a device.

Such spray devices are designed mainly for treating illnesses or conditions affecting the nasopharyngeal region (colds, rhinitis, sinusitis, etc.).

A conventional spray device comprises a container of active liquid, which container is equipped with pressurizing and/or measuring-out means serving to cooperate with a dispenser head. The head is provided with at least one expulsion duct opening out at its outer end in a spray nozzle and communicating at its inner end with the container via the pressurizing means.

Unfortunately, the head of such a spray device is provided with a single applicator only, so that, in order to apply the treatment, it is necessary to spray successively into each nostril while simultaneously blocking off the other nostril.

BRIEF SUMMARY OF THE INVENTION

An object of the present invention is to solve that technical problem satisfactorily.

The invention achieves this object by means of a nasal spray device of the above type, in which the dispenser head comprises two juxtaposed applicators, each of which is provided with at least one expulsion duct, the ends of the applicators being separated by a distance that corresponds substantially to the mean spacing between the nostrils, and the applicators being fixed to a base for coupling them to the container.

In a preferred embodiment, the two applicators are identical, each of them being provided with a respective expulsion duct which extends axially at least in its end portion.

According to an advantageous characteristic, the expulsion ducts of the two applicators merge at the bottom to form a single feed duct.

In a first variant, the duct is constituted by a central bore in said base.

In a second variant, the feed duct is constituted by a central sleeve that projects into said base.

In an advantageous embodiment, said head is made up of a first part carrying the two applicators and designed to be assembled together with a second part carrying the base.

Preferably, the two parts then define between them the bottom portions of the expulsion ducts.

In another variant, the first part is provided with an outer bottom skirt serving to clamp radially and in leaktight manner onto a cylindrical inner bearing surface provided at the top of the second part.

In another variant, the bottom face of the first part and/or the top face of the second part is/are provided with a groove/respective grooves defining at least in part the walls of the bottom portions of the expulsion ducts.

According to another characteristic, said base supports two column-shaped cores serving to be engaged axially into the end portions of the expulsion ducts so as to define annular cross-sections.

According to yet another characteristic, the bottom portions of the expulsion ducts slope relative to the axes of the applicators.

In an advantageous configuration, the two applicators are of substantially frustoconical profile with curved end edges.

The spray device of the invention is particularly ergonomic and makes it possible to improve and to simplify the therapeutic treatment.

The two-applicator dispenser head is also suitable for use with conventional pressurizing means and containers without it being necessary to modify them in any way.

In addition, the embodiment comprising only two parts is particularly easy to manufacture and assemble, which makes it very reliable and very low in cost.

Thus, regardless of the form of the pressurizing and measuring-out means, the volume of active liquid delivered is divided into two flows via the two-applicator head, which makes it possible to treat both nostrils simultaneously.

BRIEF DESCRIPTION OF THE DRAWINGS

The invention will be better understood on reading the following description accompanied by the drawings, in which.

DETAILED DESCRIPTION OF THE INVENTION

The nasal spray device shown in the Figures includes a container R containing an active liquid.

The container R is equipped with pressurizing and/or measuring-out means P, such as a pump, serving to co-operate with a dispenser head T.

Figure 1A:
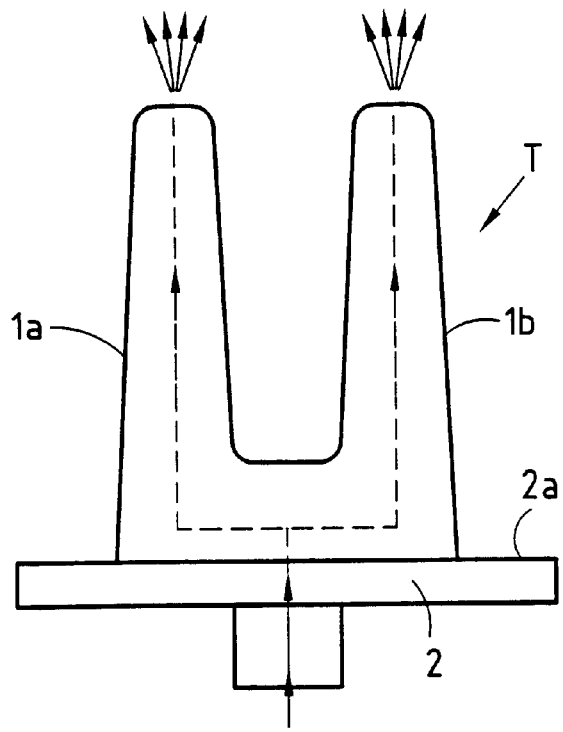
FIGS. 1a and 1b are elevation views of an embodiment of the spray device of the invention shown respectively from the front and from the side.
Figure 1B:
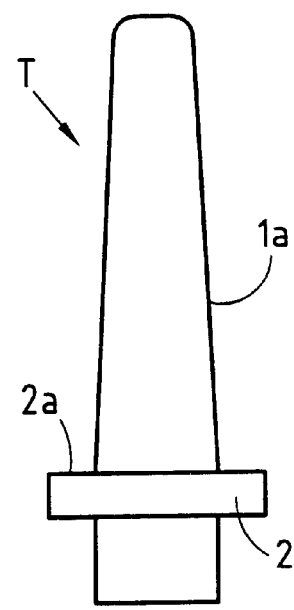
Figure 3:
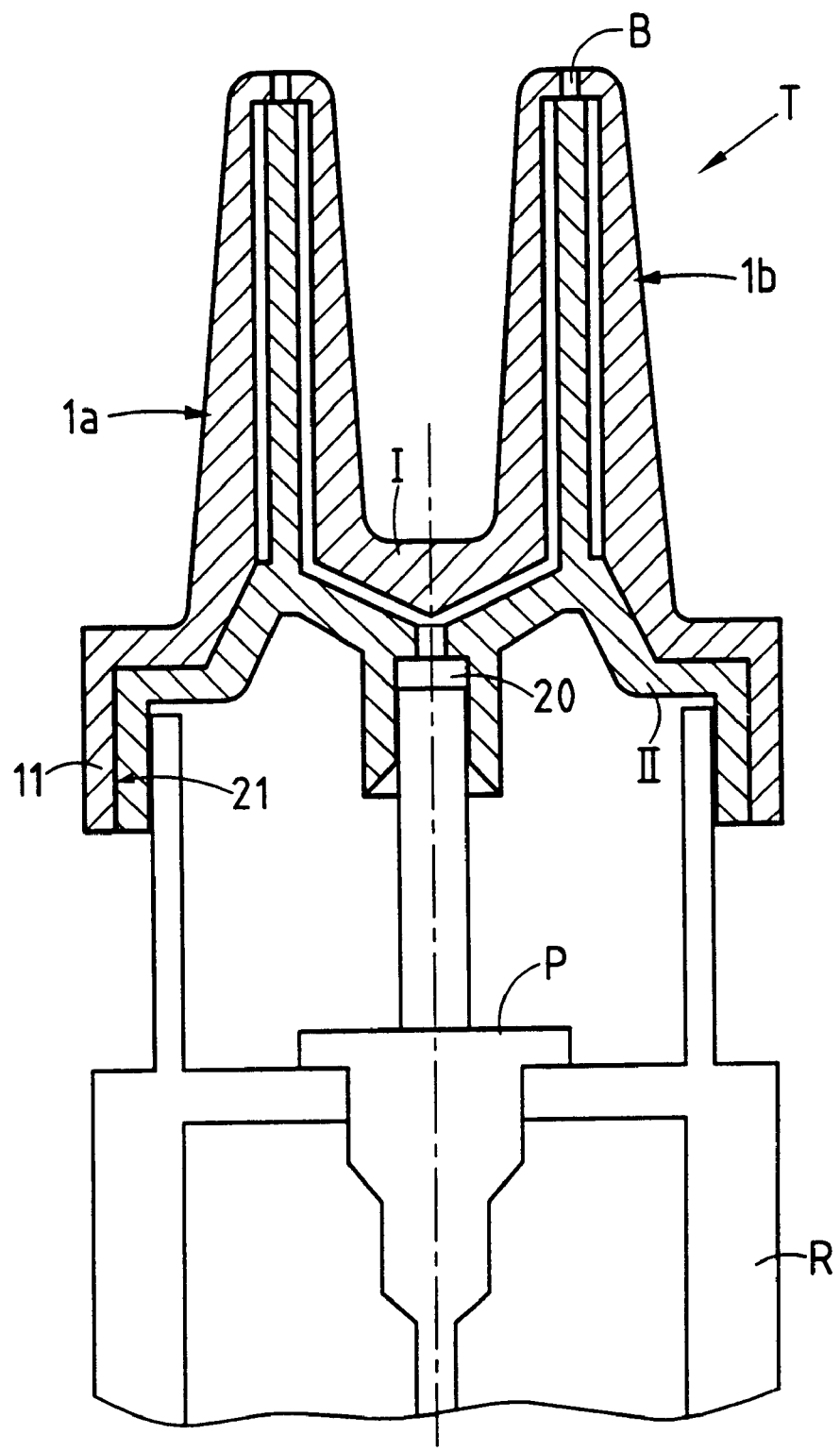
FIG. 3 is a section view of the dispenser head of another embodiment of the invention, as mounted on a container.

The head T is conventionally provided with at least one expulsion duct opening out at its outer end in a spray nozzle (not shown in FIGS. 1a and 1b), and communicating at its inner end with the container R via the pressurizing means P (shown in FIG. 3).

In the invention, the head T comprises two applicators 1a, 1b juxtaposed and fixed to a base 2 via which they are coupled to the container R.

The ends of the applicators 1a, 1b are separated by a distance corresponding substantially to the mean spacing between the nostrils.

In the embodiments shown in the figures, the two applicators 1a, 1b are identical, each of them having a substantially frustoconical profile with curved end edges facilitating insertion into the nostrils.

By pressing manually against the flat margins 2a of the base 2, it is possible to actuate the pressurizing and/or measuring-out means P, thereby causing the active liquid to be sprayed into the nostrils via the expulsion ducts in the applicators 1a, 1b and via the nozzles.

Figure 2:
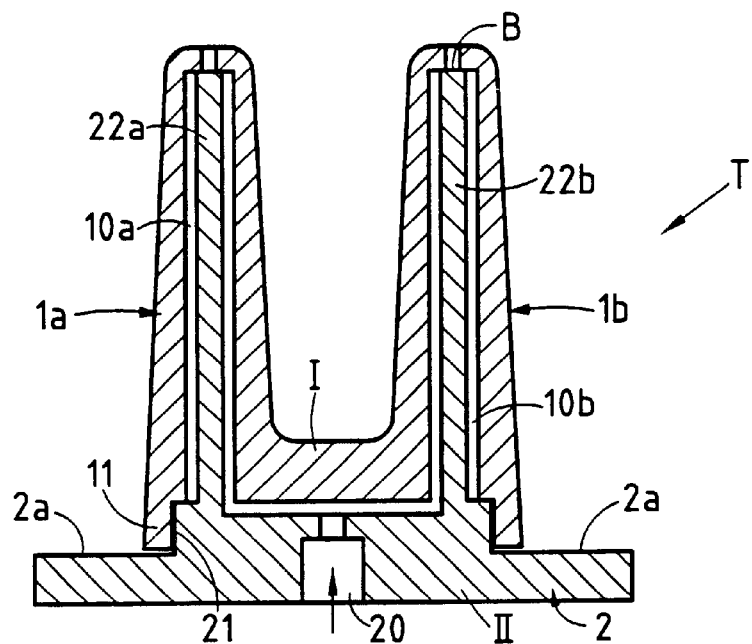
FIG. 2 is a section view of the dispenser head of the embodiment shown in FIGS. 1a and 1b.

In the embodiment shown in section in FIGS. 2 and 3, each applicator 1a, 1b is provided with an expulsion duct 10a, 10b that extends substantially axially at least in the end portion, upstream from the spray nozzle B.

The expulsion ducts 10a, 10b of the two applicators 1a, 1b merge at the bottom to form a single feed duct 20.

In FIG. 2, the feed duct 20 is constituted by a central bore in the base 2, and in FIG. 3 it is constituted by a central sleeve projecting into said base 2.

The dispenser head T is made up of a first part I carrying the two applicators 1a, 1b and designed to be assembled together with a second part II carrying the base 2

The first part I is provided with an outer bottom skirt 11 serving to clamp radially and in leaktight manner onto an inner cylindrical bearing surface 21 provided at the bottom of the second part II.

Where applicable the assembly may be supplemented by locking, e.g. in the form of snap-fastening the parts I and II together.

The two parts I, II define between them the bottom or upstream portions of the expulsion ducts 10a, 10b.

For this purpose, the bottom face of the first part I and/or the top face of the second part II is/are provided with a groove/respective grooves defining at least in part the walls of the bottom or upstream portions of the expulsion ducts once the two parts I, II have been assembled together.

When each of the parts I, II is provided with a respective groove, the two grooves are formed so that they face each other with their edges touching so as to guarantee that the assembly is leaktight.

The base 2 carries two column-shaped cores 22a, 22b serving to be engaged axially into the end portions of the expulsion ducts 10a, 10b so as to define annular cross-sections.

In the embodiment shown in FIG. 3, the bottom portions of the expulsion ducts 10a, 10b slope relative to the axes of the applicators so as to facilitate the expulsion of the active liquid and or the return of any surplus liquid to recovery or removal means (not shown).

What is claimed is:

1. A nasal spray dispenser head for connecting to a container containing a pressurized liquid comprising:

a first part defining an outer bottom skirt and a pair of applicators, each of said applicators includes an expulsion duct extending along an axis of said applicator to an exposed end defining a spray nozzle of said expulsion duct; and a second part defining a cylindrical bearing surface, a base and a pair of column-shaped cores extending vertically above and perpendicular to said base;

wherein said first and second parts are coupled such that said outer bottom skirt radially clamps said cylindrical bearing surface and each of said column-shaped cores co-axially extends through a respective one of said expulsion ducts to define an annular passage generally extending from said base to a respective one of said spray nozzles, whereby liquid from said container may pass through said annular passages and be discharged from said spray nozzles.

2. The nasal spray dispenser head according to claim 1, wherein the two applicators are similarly shaped.

3. The nasal spray dispenser head according to claim 1 wherein a single feed duct is a central bore formed by said base and positioned along a central axis generally parallel with said pair of column-shaped cores.

4. The nasal spray dispenser head according to claim 3 wherein said single feed duct comprises a central sleeve projecting into said base.

5. The nasal spray dispenser head according to claim 1 wherein the cross-section of each of said applicators gradually tapers along a length from said outer bottom skirt to said spray nozzles.

6. The nasal spray dispenser head according to claim 1 wherein each of said two applicators have a generally conical profile including curved end edges located near said spray nozzles.

* * * * *